United States Patent
Hayes et al.

(10) Patent No.: US 8,789,427 B2
(45) Date of Patent: Jul. 29, 2014

(54) METHOD AND APPARATUS FOR TESTING LOAD-BEARING CAPACITY

(71) Applicant: Loadtest, Inc., Gainesville, FL (US)

(72) Inventors: John A. Hayes, Gainesville, FL (US); William G. Ryan, Gainesville, FL (US); Nicholas K. Yankopolus, Gainesville, FL (US)

(73) Assignee: Loadtest, Inc., Gainesville, FL (US)

( * ) Notice: Subject to any disclaimer, the term of this patent is extended or adjusted under 35 U.S.C. 154(b) by 0 days.

(21) Appl. No.: 13/897,612

(22) Filed: May 20, 2013

(65) Prior Publication Data

US 2013/0247679 A1     Sep. 26, 2013

Related U.S. Application Data

(63) Continuation of application No. 13/110,756, filed on May 18, 2011, now Pat. No. 8,443,677.

(60) Provisional application No. 61/345,793, filed on May 18, 2010.

(51) Int. Cl.
  *G01L 1/00* (2006.01)
  *G01N 3/00* (2006.01)
  *E02D 5/22* (2006.01)

(52) U.S. Cl.
  USPC .................. 73/786; 73/768; 73/803; 405/233

(58) Field of Classification Search
  USPC ............. 73/768, 786, 803; 405/228, 233, 235
  See application file for complete search history.

(56) References Cited

U.S. PATENT DOCUMENTS

| | | | |
|---|---|---|---|
| 3,960,008 A | 6/1976 | Goble et al. | |
| 4,052,884 A | 10/1977 | Milberger et al. | |
| 4,614,110 A | 9/1986 | Osterberg | |
| 5,099,696 A | 3/1992 | Yabuuchi | |

(Continued)

FOREIGN PATENT DOCUMENTS

| | | |
|---|---|---|
| DE | 3424776 A1 | 1/1986 |
| RU | 2102562 C1 | 1/1998 |
| SU | 1502720 A1 | 8/1989 |
| WO | WO 2006/015278 | 2/2006 |

OTHER PUBLICATIONS

U.S. Department of Transportation, "Development of Geotechnical Resistance Factors and Downdrag Load Factors for LRFD Foundation Strength Limit State Design," Publication No. FHWA-NHI-05-052, Feb. 2005.

*Primary Examiner* — Lisa Caputo
*Assistant Examiner* — Punam Roy
(74) *Attorney, Agent, or Firm* — Saliwanchik, Lloyd & Eisenschenk

(57) ABSTRACT

In an embodiment, a hydraulic jack is provided having a first portion and a second portion. The first portion attached to a first section of a structure and the second portion attached to a second section of the structure. When a pressurized fluid is forced between the first portion and the second portion, a load is transferred to the first section and the second section by the pressure of the fluid on the first portion and the second portion. The first section and the second section are forced apart by the load, thus creating or enlarging at least one void in the structure. The pressurized fluid fills or partially fills one or more of the at least one void, thereby increasing the surface area effectively normal to the direction of the load in contact with the pressurized fluid.

12 Claims, 10 Drawing Sheets

(56) References Cited

U.S. PATENT DOCUMENTS

| | | |
|---|---|---|
| 5,172,587 A | 12/1992 | Long |
| 5,402,667 A | 4/1995 | Atkinson et al. |
| 5,576,494 A | 11/1996 | Osterberg |
| 5,581,013 A | 12/1996 | Frederick |
| 5,608,169 A | 3/1997 | Fujioka et al. |
| 6,371,698 B1 | 4/2002 | Beck, III et al. |
| 6,869,255 B1 | 3/2005 | Beck, III et al. |
| 6,942,429 B1 | 9/2005 | Beck, III et al. |
| 7,353,714 B2 | 4/2008 | England et al. |
| 7,380,462 B2 | 6/2008 | Choi et al. |
| 7,832,280 B2 | 11/2010 | Hayes |
| 8,397,583 B2 | 3/2013 | Hayes et al. |
| 8,443,677 B2 * | 5/2013 | Hayes et al. .................. 73/786 |
| 2008/0141781 A1 | 6/2008 | Hayes |
| 2011/0056303 A1 | 3/2011 | Hayes |
| 2011/0283805 A1 | 11/2011 | Hayes et al. |

* cited by examiner

METHOD AND APPARATUS FOR TESTING LOAD-BEARING CAPACITY

CROSS-REFERENCE TO RELATED APPLICATIONS

The present application is a continuation of U.S. patent application Ser. No. 13/110,756, filed May 18, 2011, which claims the benefit of U.S. Provisional Patent Application Ser. No. 61/345,793, filed May 18, 2010, both of which are hereby incorporated by reference herein in their entirety, including any figures, tables, or drawings

BACKGROUND OF INVENTION

Drilled shafts or piers are often used in the deep foundation industry because they provide an economical alternative to other types of deep foundations. Drilled piers are typically formed by excavating a cylindrical borehole in the ground and then placing reinforcing steel and fluid concrete in the borehole. The excavation may be assisted by the use of drilling fluids, casements or the like. When the concrete hardens, a structural pier suitable for load bearing results. These piers may be several feet in diameter and 50 feet or more deep. They are typically designed to support axial and tensile compressive loads.

Piles, usually made out of concrete, are generally used to form the foundations of buildings or other large structures. A pile can be considered a rigid or a flexible pile. The purpose of a pile foundation is to transfer and distribute load. Piles can be inserted or constructed by a wide variety of methods, including, but not limited to, impact driving, jacking, or other pushing, pressure (as in augercast piles) or impact injection, and poured in place, with and without various types of reinforcement, and in any combination. A wide range of pile types can be used depending on the soil type and structural requirements of a building or other large structure. Examples of pile types include wood, steel pipe piles, precast concrete piles, and cast-in-place concrete piles, also known as bored piles, augercast piles, or drilled shafts. Augercast piles are a common form of bored piles in which a hollow auger is drilled into the ground and then retracted with the aid of pressure-injected cementatious grout at the bottom end, so as to leave a roughly cylindrical column of grout in the ground, into which any required steel reinforcement is lowered. When the grout sets, the pile is complete. Piles may be parallel sided or tapered. Steel pipe piles can be driven into the ground. The steel pipe piles can then be filled with concrete or left unfilled. Precast concrete piles can be driven into the ground. Often, the precast concrete is prestressed to withstand driving and handling stresses. Cast-in-place concrete piles can be formed as shafts of concrete cast in thin shell pipes that have been driven into the ground. For the bored piles, a shaft can be bored into the ground and then filled with reinforcement and concrete. A casing can be inserted in the shaft before filling with concrete to form a cased pile. The bored piles, cased and uncased, and augercast, can be considered non-displacement piles.

A finished structural foundation element such as a pier or pile has an axial load bearing capacity that is conventionally characterized by components of end bearing ($q_b$) and side bearing, which is a function of skin friction ($f_s$). Loads applied at the top end of the element are transmitted to the sidewalls of the element and to the bottom of the element. The end bearing capacity is a measure of the maximum load that can be supported there, and it will depend on numerous factors including the diameter of the element and the composition of the geomaterial (soil, rock, etc.) at the bottom of the shaft. The side bearing capacity is a measure of the amount of load capable of being borne by the skin friction developed between the side of the pier/pile and the geomaterial. It depends on numerous factors, including the composition of the foundation element and the geomaterial forming the side of the element, which may vary with length (depth). The sum of the end bearing and side bearing capacities generally represents the total load that can be supported by the element without sinking or slippage, which could cause destructive movements for a finished building or bridge atop the foundation.

Although it is desirable to know the maximum end bearing and side bearing for a particular pier or driven pile, it is difficult to make such measurements with a high degree of confidence. Foundation engineering principles account for these difficulties by assigning end bearing and load bearing capacities to a foundation element based on its diameter and depth, the geomaterial at the end of the element and along its side, and other factors. A safety factor is then typically applied to the calculated end bearing and side bearing capacities. These safety factors are chosen to account for the large number of unknown factors that may adversely affect side bearing and end bearing, including geomaterial stress states and properties, borehole roughness generated by the drilling process, geomaterial degradation at the borehole-shaft interface during drilling, length of time the borehole remains open prior to the placement of concrete, residual effects of drilling fluids, borehole wall stresses produced by concrete placement, and other construction-related details. For example, it is common to apply a safety factor of 2 to the side bearing so as to reduce by half the amount calculated to be borne by skin friction. Likewise, a safety factor of 3 is often applied to the calculated end bearing capacity, reflecting the foregoing design uncertainties and others. Load Resistance Factor Design (LRFD) is an alternative analysis method used to design safe and efficient structural foundations by incorporating load and resistance factors based on the known variability of applied loads and material properties.

The use of safety factors, or LRFD factors, although judiciously accounting for many of the uncertainties in drilled shaft pier construction and driving piling, often results in such foundation elements being assigned safe load capacities that are too conservative. To compensate, builders construct larger, deeper, and/or more elements than are necessary to safely support a structural load, unnecessarily increasing the time, effort and expense of constructing a suitable foundation.

As a partial solution, it has been known to directly measure the end bearing capacity and skin friction of a drilled-shaft pier. This is typically accomplished at a production site by using one or more test piles.

Osterberg (U.S. Pat. Nos. 4,614,110 & 5,576,494) discloses a parallel-plate bellows placed in the bottom of the shaft before a concrete pier is poured. The bellows are pressured up with fluid communicated through a pipe coaxial with the pier. Skin friction is determined by measuring the vertical displacement of the pier (corresponding to the movement of the upper bellows plate) as a function of pressure in the bellows. Likewise, end bearing is determined by measuring pressure against the downward movement of the lower bellows plate, as indicated by a rod affixed thereto and extending above the surface through the fluid pipe. Upon completion of the load test, the bellows are depressurized. The bellows may then be abandoned or filled with cement grout, and in the latter case becomes in essence an extension of the lower end of the pier.

In that case, the non-functioning testing cell serves as the base of the pier and may thereby compromise the integrity of the shaft. In practice, a drilled shaft employing the "Osterberg cell" is often abandoned after testing in favor of nearby shafts that do not contain a non-functioning testing cell at their base. Because it is wasteful in terms of time, materials, effort and money to abandon a formed shaft merely because it was used for testing, there remains a need for a testing cell that causes less interference with use of the shaft after testing.

BRIEF SUMMARY

Embodiments of the subject invention are directed to an apparatus and method for testing the load bearing capacity of one or more structures, such as piles, shafts, or other structures. In an embodiment, a load cell is provided that creates a void in the structure being tested. In an embodiment, the created void is used as an additional load applying area for testing of the structure. In an embodiment, the created void is filled with a pressurized fluid and, in a further specific embodiment, the pressurized fluid is a self-sealing fluid. In an embodiment, such a load cell is used to test the load bearing capacity of a pile, shaft, or other structure. In an embodiment, use of such a load cell allows the use of the pile, shaft, or other structure after testing as a foundation support structure, or production pile. In an embodiment, a ring, or annular, load cell is used. In an embodiment, use of the testing apparatus and/or method, increases the desirability of using one or more of tested piles as production piles. Embodiments of the invention can be used with a pile cast in place or drilled shaft pile.

In an embodiment of the subject invention, a method of applying a load to a structure is provided. In an embodiment, a hydraulic jack is provided incorporating a first portion and a second portion. In an embodiment, the first portion is proximate to a first section of the structure and the second portion is proximate to a second section of the structure. In an embodiment, when a pressurized fluid is injected between the first portion and the second portion, a load is transferred to the first section of the structure and the second section of the structure by the pressure of the fluid on the first portion and the second portion, respectively. In an embodiment, the first portion is attached to the first section of the structure and/or the second portion is attached to the second section of the structure. In an embodiment, the first portion and the second portion are proximate to each other before the pressurized fluid is injected between them. In an embodiment, the first portion and the second portion are separated by a separation zone before the pressurized fluid is injected between them. In an embodiment, the first section of the structure and the second section of the structure are forced apart by the load, thus creating or enlarging at least one void in the structure. In an embodiment, the pressurized fluid fills or partially fills one or more of the at least one void, thereby increasing the surface area of the first section and/or second section effectively normal to the direction of the load, or force, in contact with the pressurized fluid. In an embodiment, the increased surface area allows a greater load to be applied to the structure for the same pressure of the pressurized fluid.

In an embodiment, before the pressurized fluid is injected between the first portion and the second portion, the first section of the structure and the second section of the structure form one contiguous structure, such that when pressurized fluid is injected between the first portion and the second portion so as to cause the first portion and the second portion to move away from each other a sufficient distance the one contiguous structure separates into the first section and second section, which no longer form one contiguous structure. In a specific embodiment, grout, concrete, or other material can fill one or more of the at least one void in the structure, such that the first section of the structure and the second section of the structure once again form one contiguous structure.

In an embodiment, a self-sealing fluid is used for the pressurized fluid. In an embodiment, the self-sealing fluid fills or partially fills the one or more of the at least one void in the structure. In an embodiment, the self-sealing fluid permanently fills or partially fills the one or more of the at least one void.

BRIEF DESCRIPTION OF THE DRAWINGS

Reference will now be made in detail to the preferred embodiments of the present invention, examples of which are illustrated in the accompanying drawings. Wherever possible, the same reference numbers will be used throughout the drawings to refer to the same or like parts.

DETAILED DISCLOSURE OF THE INVENTION

Figure 1A:
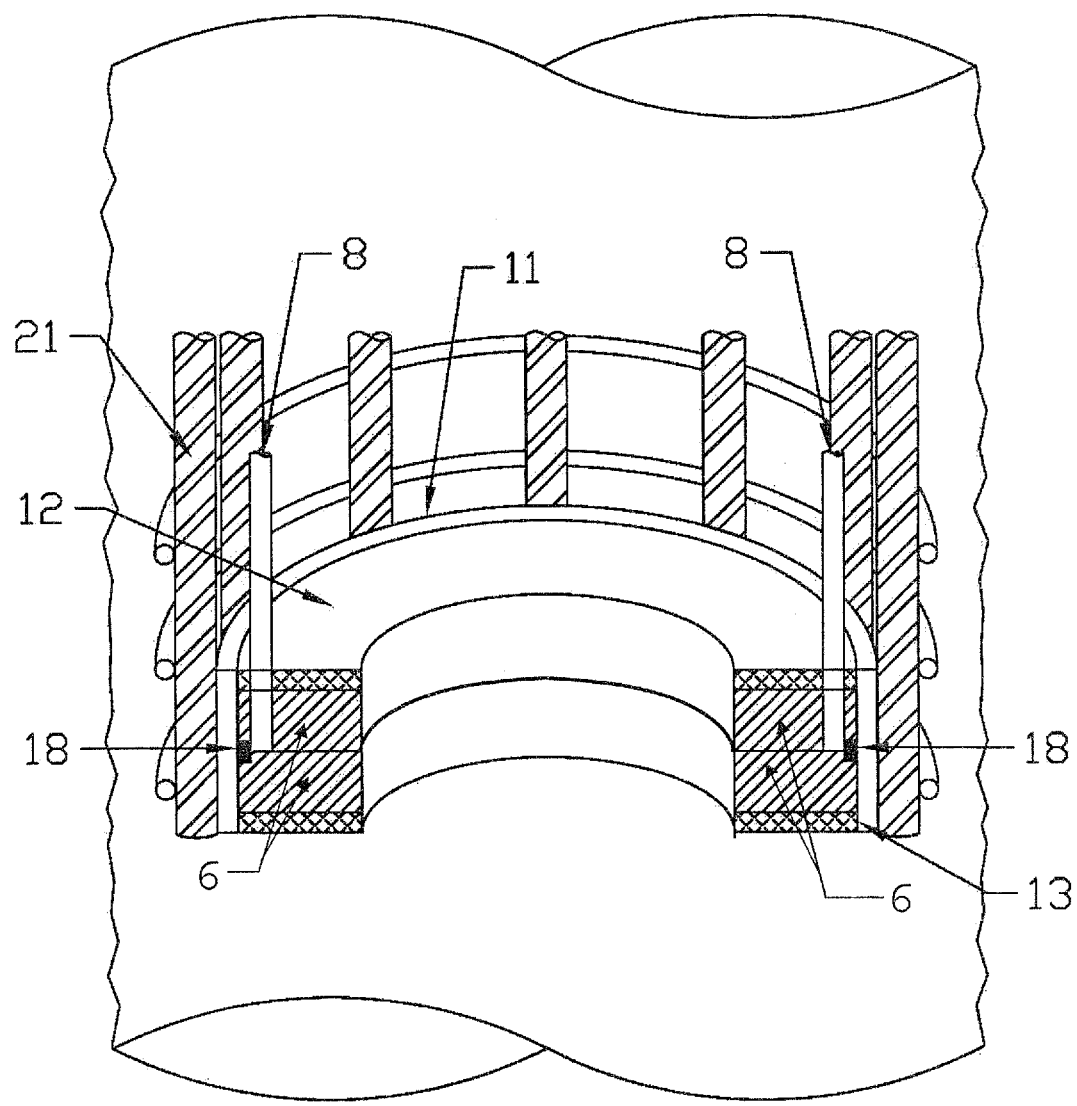
FIGS. 1A-1B show a sectional view of a specific embodiment of the present invention.

Embodiments of the subject invention are directed to an apparatus and method for testing the load bearing capacity of one or more structures, such as piles, shafts, or other structures. In an embodiment, a load cell is provided that creates a void in the structure being tested. In an embodiment, the created void is used as an additional load applying area for testing of the structure by filling the void with pressurized fluid. In a specific embodiment, the created void is filled with a self-sealing fluid. In an embodiment, such a load cell is used to test the load bearing capacity of at least one pile, shaft, or other structure, in which, for example, the load cell is incorporated into. In an embodiment, use of such a load cell allows the use of one or more of the at least one pile, shaft, or other structure after testing as a foundational structure such as a production pile. In an embodiment, a ring, or annular, load cell is used. In an embodiment, use of the testing apparatus and/or method, increases the desirability of using one or more of tested piles as production piles. Embodiments of the invention can be used with a pile cast in place or drilled shaft pile.

An embodiment of the invention relates to a method of applying a load to a structure. In an embodiment, a hydraulic jack is provided incorporating a first portion and a second portion. In an embodiment, the first portion is positioned proximate to a first section of the structure and the second portion is positioned proximate to a second section of the structure. In an embodiment, when a pressurized fluid is injected between the first portion and the second portion, a load is transferred to the first section of the structure by the first portion and a load is transferred to the second section of the structure by the second portion, via the pressure of the fluid on the first portion and the second portion and/or via the pressure of the fluid on the first section and/or second section. In an embodiment, the first portion is attached to the first section of the structure and/or the second portion is attached to the second section of the structure. In an embodiment, the first portion and the second portion are proximate to each other before the pressurized fluid is injected between them. In an embodiment, the first portion and the second portion are separated by a separation zone before the pressurized fluid is injected between them. In a specific embodiment, the first section of the structure and the second section of the structure are forced apart by the load, thus creating or enlarging at least one void in the structure. In a further specific embodiment, the pressurized fluid fills or partially fills one or more of the at least one void, thereby increasing the surface area of the first section and/or second section effectively normal to the direction of the load, of force, in contact with the pressurized fluid. In an embodiment, the increased surface area allows a greater load to be applied to the structure for the same pressure of the pressurized fluid.

Various hydraulic fluids can be used with the subject invention. In an embodiment, a mineral oil based fluid is used. In an embodiment, a water based fluid is used. In an embodiment, the hydraulic fluid has low compressibility, low volatility, and/or low foaming tendency. The hydraulic fluid can have lubricating properties so as to lubricate components of the assembly. In an embodiment, a self-sealing fluid is used. The self-sealing fluid can be used to seal any leaks in the assembly. The self-sealing fluid can be used to temporarily or permanently fill voids or cracks as discussed below. In an embodiment, the self-sealing fluid results in a permanent, flexible seal. In a specific embodiment, the self-sealing fluid is a chemical mix of friendly fibers, particulates, binders, polymers, and/or congealing agents that intertwine and clot to form an impervious seal. Commercial compounds with similar properties that can be used in embodiments of the subject invention include, but are not limited to, Slime® and AMERSEAL®. Other hydraulic fluids are known in the art and can be used in embodiments of the subject invention.

In an embodiment, before the pressurized fluid is injected between the first portion and the second portion, the first section of the structure, or pile, and the second section of the structure, or pile, form one contiguous structure. Upon injection of a sufficient amount of pressurized fluid between the first portion and the second portion, the first and second portion can move away from each other, resulting in the separation of the one contiguous structure into a first section and a second section. The separation of the one contiguous structure into a first section and a second section creates a void between the first section and the second section, into which the pressurized fluid can flow. Advantageously, introduction of the pressurized fluid into the void between the first, or top, section of the pile allows the pressurized fluid to apply forces to the walls of the void (surfaces of the first and second sections) so as to apply a much larger force for the same pressure of pressurized fluid. This allows the seals to perform much better and/or higher forces to be achieved. At some point a filler material, such as grout or concrete can replace the pressurized fluid, or the pressurized fluid can be a grout, concrete, or other hardening fluid, and the grout, concrete, or other hardening fluid can harden in the one or more of the at least one void in the structure, such that the first section of the structure and the second section of the structure, along with the hardened filler material once again form one contiguous structure.

The fluid used to apply force to separate the first portion and the second portion and fill one or more voids between the first section of pile and the second section of pile can be replaced with a fluid that hardens or can harden itself. Preferably, a self-sealing fluid is used as the pressurized fluid to help seal any leaks that may develop. In an embodiment, a cementatious or other fluid that hardens, such as chemical type hardening fluids, can be used as the pressurized fluid. The cementatious fluid can have the amount of retarder used varied, and/or the chemical type hardening fluids can have the amount of hardener used varied, in order to control how long it takes for the fluid used as the pressurized fluid to harden. In various embodiments, the time for the pressurized fluid to harden can be selected and controlled to be at least 1 hour and not more than 12 hours; at least 1 hour and not more than 24 hours; at least 1 day and not more than 7 days; and at least 7 days and not more than 30 days, such that time is allowed to accomplish the required testing and other necessary actions and that the fluid hardens in time to use the pile for the desired function. In a specific embodiment, one part of an epoxy can be used as the pressurized fluid until the testing is accomplished and then the other part of the epoxy can be added when it is time to have the fluid harden.

In an embodiment, the structure is a cast form of concrete or other material. The form can be cast around or partially around the hydraulic jack. In an embodiment, the structure is an engineering pile. The hydraulic jack can be positioned in the structure using a rebar cage or other structure known in the art. As an example, the hydraulic jack can be attached to the rebar cage using a bracket, clamp, or other structure known in the art. In an embodiment, the first portion of the hydraulic jack is attached to the rebar cage. In an embodiment, the second portion of the hydraulic jack is attached to the rebar cage. When the pressurized fluid is injected between the first portion and the second portion, the first portion can move relative to the second portion in a direction of expansion of the jack while the second portion remains in the same location. In another embodiment, the second portion moves relative to the first portion in a direction approximately opposite to the direction of expansion of the jack. In a further embodiment, both the first portion and the second portion move as the first portion and second portion move relative to each other.

In a specific embodiment, when the pressurized fluid is injected between the first portion and the second portion, the first portion maintains approximately the same relative position with respect to the second portion in one or both directions orthogonal to the direction of expansion of the jack. In an embodiment, when the first section of the structure and the second section of the structure are forced apart by the load, the first section moves relative to the second section in the direction of expansion of the structure while the second section remains still. In another embodiment, the second section moves relative to the first section in the direction of expansion of the structure while the first section remains still. In a further embodiment, both the first section and the second section move when the first section and second section move relative to each other. In an embodiment, when the first section of the structure and the second section of the structure are forced apart by the load, the first section maintains approximately the same relative position with respect to the second section in one or both directions orthogonal to the direction of expansion of the structure. In an embodiment, the direction of expansion of the structure is approximately the same as the direction of expansion of the jack.

In a particular embodiment, the structure is a vertical pile, the first section is a top section of the pile, the second section is a bottom section of the pile, the hydraulic jack is positioned vertically in the pile, such that the first portion of the hydraulic jack is a top portion and the second portion of the hydraulic jack is a bottom portion. The top portion of the hydraulic jack can be positioned below the top section of the pile and the bottom portion of the hydraulic jack is positioned above the bottom section of the pile. In a preferred embodiment, a portion of the cross-sectional area of the top portion and a portion of the cross-sectional area of the bottom portion is open, such that material, such as concrete, grout, and/or other materials, can pass through the open portion of the cross-sectional area of the top portion and the open portion of the cross-sectional area of the bottom portion. In an embodiment, such material can pass from above the top portion to below the bottom portion. In an embodiment, such material can pass from below the bottom portion to above the top portion.

In an embodiment, the hydraulic jack and/or the rebar cage is lowered into slurry water, concrete or another material, and the material passes through the open portion of the cross-sectional area of the bottom portion and the open portion of the cross-sectional area of the top portion as the apparatus sinks into the material. The material can be passed through the open portion of the cross-sectional area of the top portion and the open portion of the cross-sectional area of the bottom portion, and can fill the open portion of the jack from above the jack to below the jack during formation of the pile, such that the top section of the pile and the bottom section of the pile are contiguous through the open portion of the cross-sectional area of the top portion and the open portion of the cross-sectional area of the bottom portion.

In an embodiment, when a pressurized fluid is injected between the top portion and the bottom portion of the jack, a load is transferred to the top section of the pile and the bottom section of the pile by the pressure of the fluid on the top portion and the bottom portion, such that the top portion pushes up on the top section of the pile and/or the bottom portion pushes down on the bottom section of the pile. The top portion and the bottom portion are proximate to each other before the pressurized fluid is injected between them. In a specific embodiment, the top portion and the bottom portion are separated by a separation zone before the pressurized fluid is injected between them. In a further embodiment, the top section of the pile and the bottom section of the pile are forced apart by the load, thus creating or enlarging at least one void in the pile. One or more of the at least one void can be created in the portion of the pile contiguous through the open portion of the cross-sectional area of the top portion and the open portion of the cross-sectional are of the bottom portion of the pile. In an embodiment, the pressurized fluid fills or partially fills one or more of the at least one void, thereby increasing the surface area, effectively normal to the direction of the load, in contact with the pressurized fluid. In an embodiment, the increased surface area allows a greater load to be applied to the pile for the same pressure of the pressurized fluid.

In an embodiment, before the pressurized fluid is injected between the top portion and the bottom portion, the top section of the pile and the bottom section of the pile form one contiguous pile. A self-sealing fluid can be used for the pressurized fluid. In an embodiment, the self-sealing fluid fills or partially fills the one or more of the at least one void in the pile. The self-sealing fluid can permanently fill or partially fill the one or more of the at least one void. Once the concrete, grout or other structural material sets, the top section of the pile and the bottom section of the pile once again form one contiguous pile.

The hydraulic jack can be positioned in the pile using a rebar cage or other structure known in the art. In an embodiment, the hydraulic jack is attached to the rebar cage using a bracket, clamp, or other structure known in the art. In a specific embodiment, the top portion of the hydraulic jack is attached to the rebar cage. In an alternative embodiment, the bottom portion of the hydraulic jack is attached to the rebar cage such that the jack is held at a desired vertical position in the pile, while allowing the jack to separate while allowing the rebar cage to remain in place. When the pressurized fluid is injected between the top portion and the bottom portion, the top portion can move up while the bottom portion remains fixed relative to the rebar cage, or the bottom portion moves down while the top portion remains fixed relative to the rebar cage. In further embodiments, the jack can be slidably attached to rebar cage such that the jack can slide up and down with a certain vertical region, or the rebar cage, while keeping level with respect to the horizontal plane, such that the top and/or bottom sections of the jack can slide along the rebar cage when pressurized fluid is applied to the jack. In an embodiment, when the pressurized fluid is injected between the top portion and the bottom portion, the top portion maintains approximately the same relative lateral position with respect to the bottom portion.

In an embodiment of the subject invention, there is provided an annular load testing assembly, or jack, including: a filler material capable of withstanding high pressure; an outer perimeter cylinder having an outer wall, a top wall, an optional inner wall, and an optional bottom wall, where an inner surface of the outer perimeter cylinder contacts the filler material; and one or more fluid access lines for supplying fluid to a separation zone between the filler material, the outer wall, and/or the optional inner wall. In an embodiment, the separation zone includes a membrane in contact with the filler material. Fluid can be injected into the separation zone under pressure thus expanding the separation zone. In an embodiment, a passage is formed in the filler material, inner wall, bottom wall, or other component, such that the injected fluid can reach other components of the assembly and/or beyond the assembly itself. Such a passage can be intentionally formed.

In an embodiment of the subject invention, there is provided an annular load testing assembly, or jack, including: a filler material capable of withstanding high pressure; an outer perimeter u-shaped cylinder having an outer wall, an inner wall, a top wall; an inner perimeter u-shaped cylinder having an outer wall, an inner wall and a bottom wall, where an inner surface of the outer wall of the outer perimeter cylinder contacts the outer surface of the outer wall of the inner perimeter cylinder and an inner surface of the inner wall of the outer perimeter u-shaped cylinder contacts the outer surface of the inner wall of the inner perimeter u-shaped cylinder; and one or more fluid access lines for supplying a pressurized fluid to a separation zone between the filler material. The separation zone may include a membrane in contact with the filler material. Fluid can be injected into the separation zone under pressure thus expanding the separation zone. In an embodiment, a passage is formed in the filler material, inner wall, bottom wall, and/or other component, such that the injected fluid can reach other components of the assembly and/or beyond the assembly itself. In an embodiment, such a passage is intentionally formed.

An embodiment of the invention pertains to a method for providing piles for a structure, the method including: incorporating an annular jack assembly into one or more construction piles, inputting pressurized fluid to the jack assembly so as to separate each construction pile into a top section and a bottom section such that a crack and/or void is created between the top section and bottom section of the construction pile; and filling the crack and/or void formed between the top section and bottom section of the construction pile with grout, concrete, and/or other structural material. Such crack and/or void can serve as an extension of a separation zone within the jack in order to provide additional surface area effectively normal to the direction of the load in contact with the pressurized fluid so as to achieve a greater force for the same pressure of the pressurized fluid. If desired, load testing of the construction pile can be performed when the pressurized fluid is inputted to the jack, such as after the construction pile separates into a top section and a bottom section.

In a particular embodiment, an annular assembly as described herein can be used in production piles (e.g., piles used as a foundation of a structure). The annular assembly can be inexpensively manufactured. The annular assembly can allow concrete and/or grout to pass through the assembly, while in place, during casting of the pile.

In an embodiment, during construction, the subject annular assembly, or ring cell, can be placed in most, or all, production piles, if desired. The ring cell placed in one or more piles can remain in the one or more piles after testing. In an embodiment, a cured grout, concrete, or other structural material remains in the ring cells and/or crack and/or void between the top section and bottom section of the pile after the jack is expanded so as to separate the pile into a top section and bottom section and, optionally, load testing the pile. In one embodiment, at least 10% of the production piles can have ring cells. In other embodiments, at least 50%, at least 80%, at least 90%, or 100% of the production piles can have ring cells.

Piles, having ring cells, to be used as production piles can be designed using a lower factor of safety or an increased resistance factor (RF), because the piles can be tested such that the load bearing capacity of the piles to be used can be more accurately predicted. In one embodiment, the RF can be 0.6. In another embodiment, the RF can be 0.9. In an embodiment, the ring cells can be made cheaply because the pieces can be made of stamped material, or alternatively preformed or pre-cast materials. Advantageously, in embodiments, the ring cell walls can be made by stamping material, because of the ring cell's curved shape. In a particular embodiment, a curved shape ring cell can allow for stamping pieces out instead of welding and machining because the tolerances are not as tight.

Furthermore, the components of the ring cells can be selected for cost and simplicity. For example, a ring cell can incorporate stamped sheet metal, filler material that can withstand high pressures such as high strength grout, and/or rubber or fabric membranes or bladders.

It should be noted that a self-sealing high pressure fluid may be used for embodiments not incorporating a bladder. This self-sealing fluid can be used as a hydraulic fluid substitute and is typically a chemical mix of friendly fibers, binders polymers and congealing agents that intertwine and clot to form an impervious seal. A commercial compound with similar properties that can be used in an embodiment is Slime®.

It should be noted that embodiments of the subject invention can be used with one or more types of shafts and piles. In addition, one or more ring cells or annular assemblies in accordance with the invention can be used in a single pile shaft and can be located at various vertical positions along the shaft.

Figure 1B:
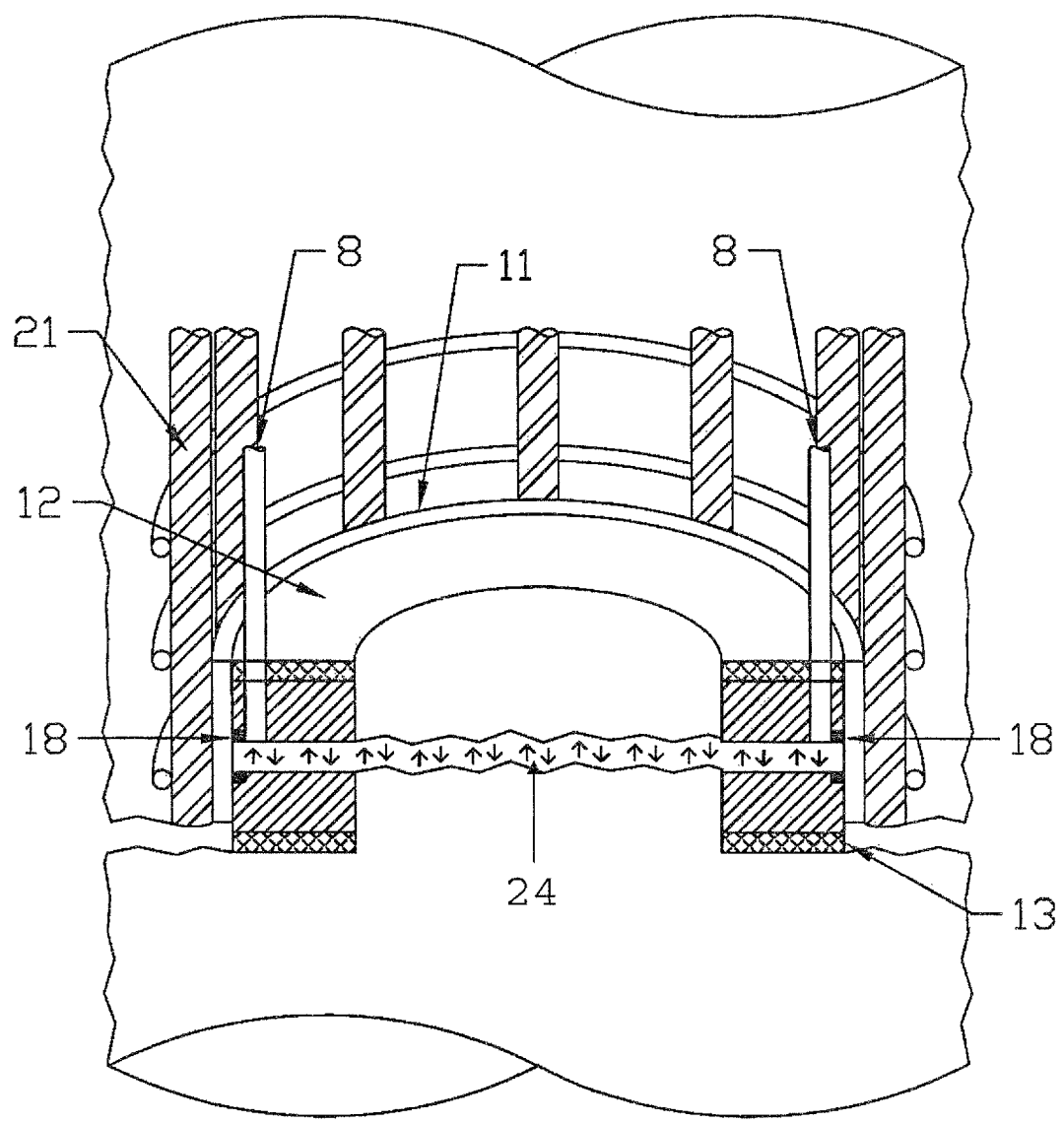

FIGS. 1A-1B show a sectional view of a specific embodiment of the present invention. In the embodiment shown, a hydraulic jack is provided including filler materials 6 in a ring shape. In an embodiment, the filler materials 6 are capable of withstanding high pressure with minimal deformation as further described below. Fluid access lines 8 are used to inject hydraulic fluid under pressure against the filler materials 6. In the embodiment shown, an outer cylinder wall 11 bounds the outside of the ring-shaped filler materials 6. The embodiment shown also includes a top plate 12 and a bottom plate 13, which further bound the filler materials 6. The embodiment shown also includes seals 18 positioned to inhibit leaking of hydraulic fluid along the outer cylinder wall 11. In an embodiment, o-rings are used for the seals 18. The hydraulic jack can be attached to a rebar cage 21. As further discussed below, various structures can be used to attach the hydraulic jack to the rebar cage 21. As shown in FIG. 1A, the center of the top plate, the center of the ring-shaped filler material 6, and the center of the bottom plate are open to allow passage of materials through the hydraulic jack. The open center can allow concrete, grout, or other structural materials to be passed through the hydraulic jack. In an embodiment, the open center is used to form a contiguous pile having portions above and below the hydraulic jack, such that a portion of such a contiguous pile passes through the open center. As shown in FIG. 1B, a pile is formed that encompasses the rebar cage 21 and the ring-shaped filler materials 6.

In the embodiment shown in FIG. 1B, hydraulic fluid is injected under pressure via fluid access lines 8. The pressure from the hydraulic fluid pushes on the ring-shaped filler materials 6, causing the filler materials 6 to separate. The filler materials 6 transfer the applied load to the pile. In the embodiment shown, the application of the load to the pile causes the pile to crack creating a void 24 in the pile. The void 24 is created in the open center of the ring-shaped filler materials 6. In the embodiment shown, the void 24 is contiguous with the separation of the filler materials 6. Thus, the hydraulic fluid can flow from the separation into the void 24. The hydraulic fluid can fill all or part of the void 24. A self-sealing fluid capable of temporarily or permanently filling all or part of the void 24 can be used. The hydraulic fluid fills or partially fills the void 24 under pressure such that the void 24 becomes an additional load applying area for applying a load to the pile. In an embodiment, use of the void 24 increases the surface area effectively normal to the direction of the load in contact with the pressurized fluid, such that the increased surface area allows a greater load to be applied to the pile. The pressurized fluid can be flushed out and replaced by pressurized grout, concrete, or other structural material, which can be allowed to cure so as to form a contiguous pile through the center of the jack. In a preferred embodiment, outer cylindrical wall 11 is designed such that the pressurized fluid will be contained within the volume formed within the outer cylindrical wall 11.

Figure 2A:
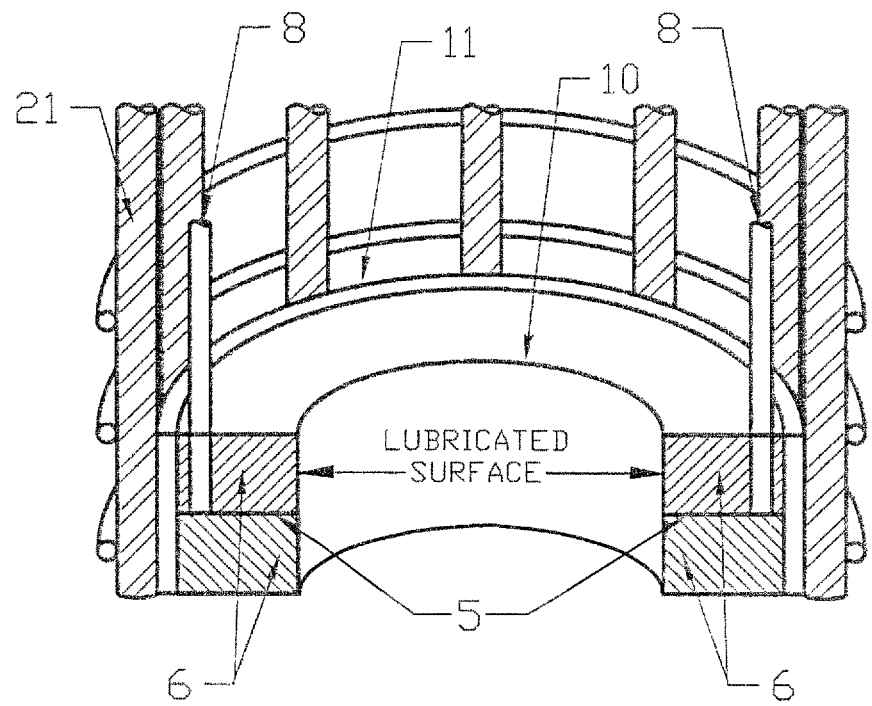
FIGS. 2A-2C show a sectional view of a specific embodiment of the present invention.
Figure 2B:
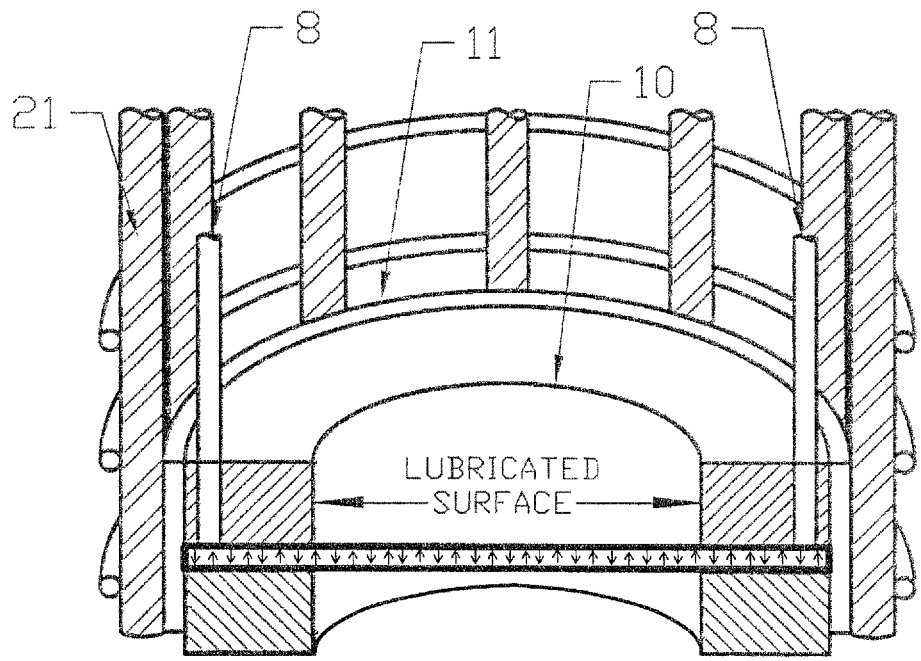

In another embodiment as shown in FIG. 2A, the ring cell can incorporate an outer cylinder wall 11. The outer cylinder wall 11 can be made of steel, high strength polymer/plastic, or other appropriate materials known in the art that are able to withstand the high pressures. A filler material 6 such as HSG can be positioned within the outer side wall 11 and more filler material 6 can be positioned below the filler material 6 used in connection with the top portion to form a bottom portion, such that the pressurized fluid is injected between the top and bottom portions. The inner surface of the outer wall can be lubricated such that the filler material 6 can slide with reduced friction from the outer wall as fluid fills between the filler materials and void 24. In an embodiment, the fluid itself provides the lubrication. The top and bottom portions of the jack can be situated within a pile such that a top surface of the top portion filler material 6 contacts the pile material above the ring cell and the bottom surface of the bottom portion filler material 6 contacts the pile material below the ring cell. One or more hydraulic fluid access lines 8 can provide fluid to the separation between the top portion and the bottom portion through the top of the filler material 6. As pressure builds, the pressurized fluid pushes against the filler material as shown in FIG. 2B and causes void 24 to be created when the pile separates into a first, top, section and a second, bottom, section, such that the pressurized fluid fills void 24. Concrete, or other materials to form the pile, can be poured through the opening in the center of the ring cell for ease of positioning of the ring cell.

Figure 3A:
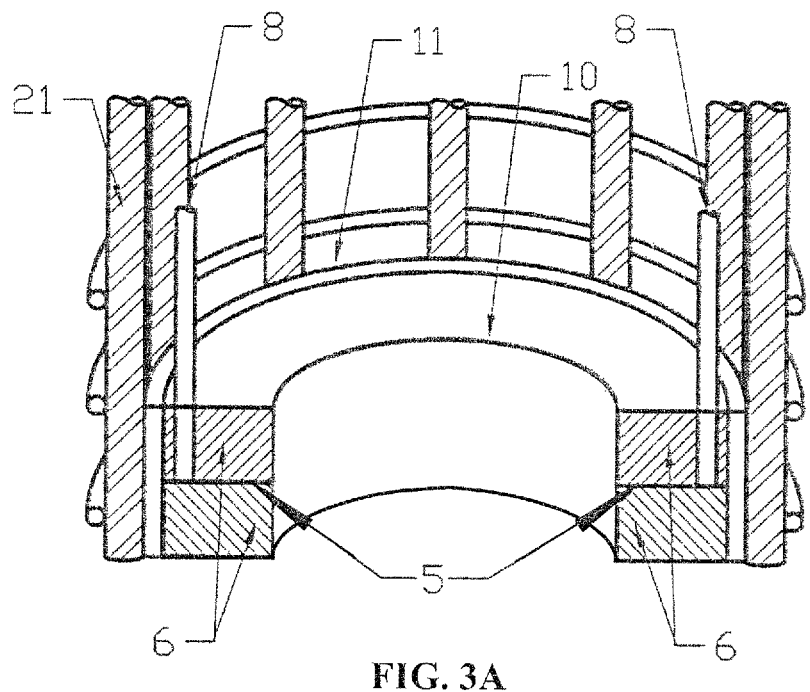
FIGS. 3A-3C show embodiments of varying cross-sectional area.
Figure 3B:
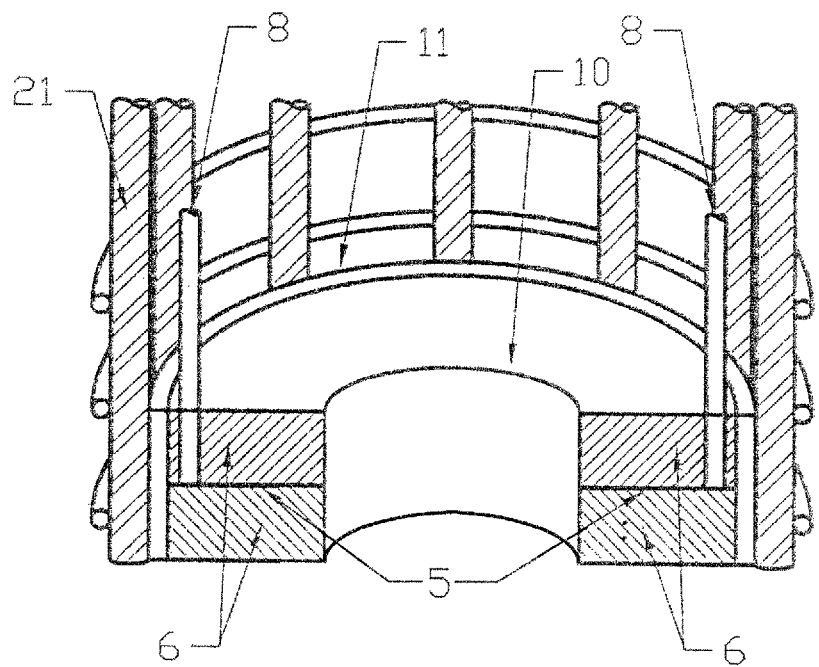
Figure 3C:
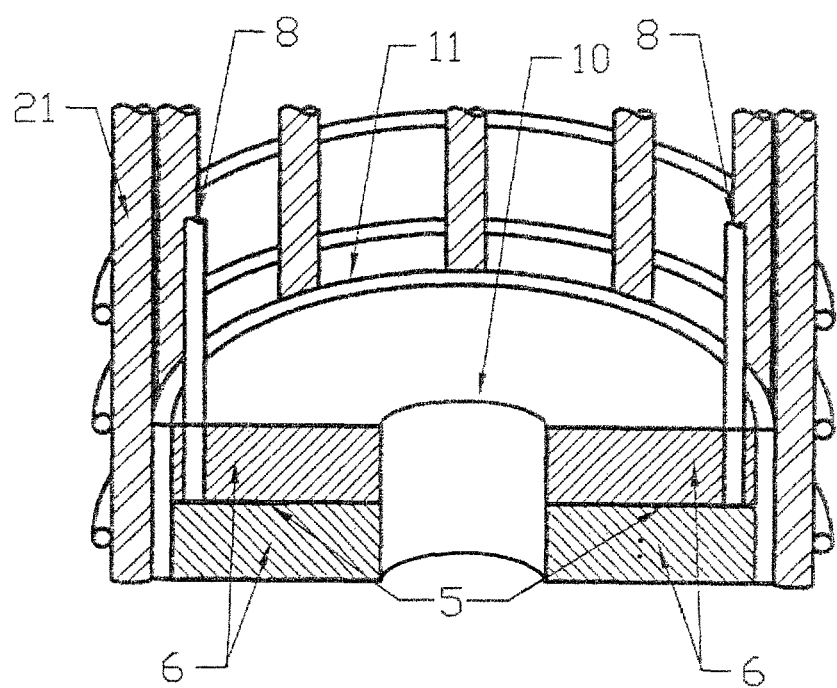

The size of the annular assembly can depend on the size of the shaft or bore hole. The outer wall of the ring cell can have a radius of a size to allow proximate location to a rebar cage while the ring cell is in a shaft. The size of the walls can be determined by the surface required to apply proper force. Embodiments with top plates and/or bottom plates can have the plates attached to the section of pile above the load cell and/or the section of the pile below the load cell. The top portion of the load cell and the bottom portion of the load cell are positioned so that when they separate their relative lateral position remains the same. In this way the section of pile above, the top portion of the cell, the bottom portion of the cell, and an optional section of the pile below the cell act as a single pile, rather than two floating pile sections. If the cell is located at the bottom of a shaft, the cell can lie on ground or, for example, on a piece of concrete, which can be six inches to one foot thick or other appropriate thickness. The open center of the ring cell allows ease of access to inject concrete, or other pile material, past the ring cell to form the portion of the pile below the ring cell. In various specific embodiments, the opening in the center of the ring cell can be at least 25%, at least 50%, and at least 75% of the cross-sectional area of the ring cell. In a specific embodiment as shown in FIG. 3C, the opening in the center of the ring cell can be at least 20% of the cross-sectional area of the ring cell to facilitate the passage of concrete through the opening. In another embodiment as shown in FIG. 3B, the opening is at least 40% of the cross-sectional area of the ring cell, and in a further specific embodiment as shown in FIG. 3A, the opening is at least 60% of the cross-sectional area of the ring cell.

Figure 5A:
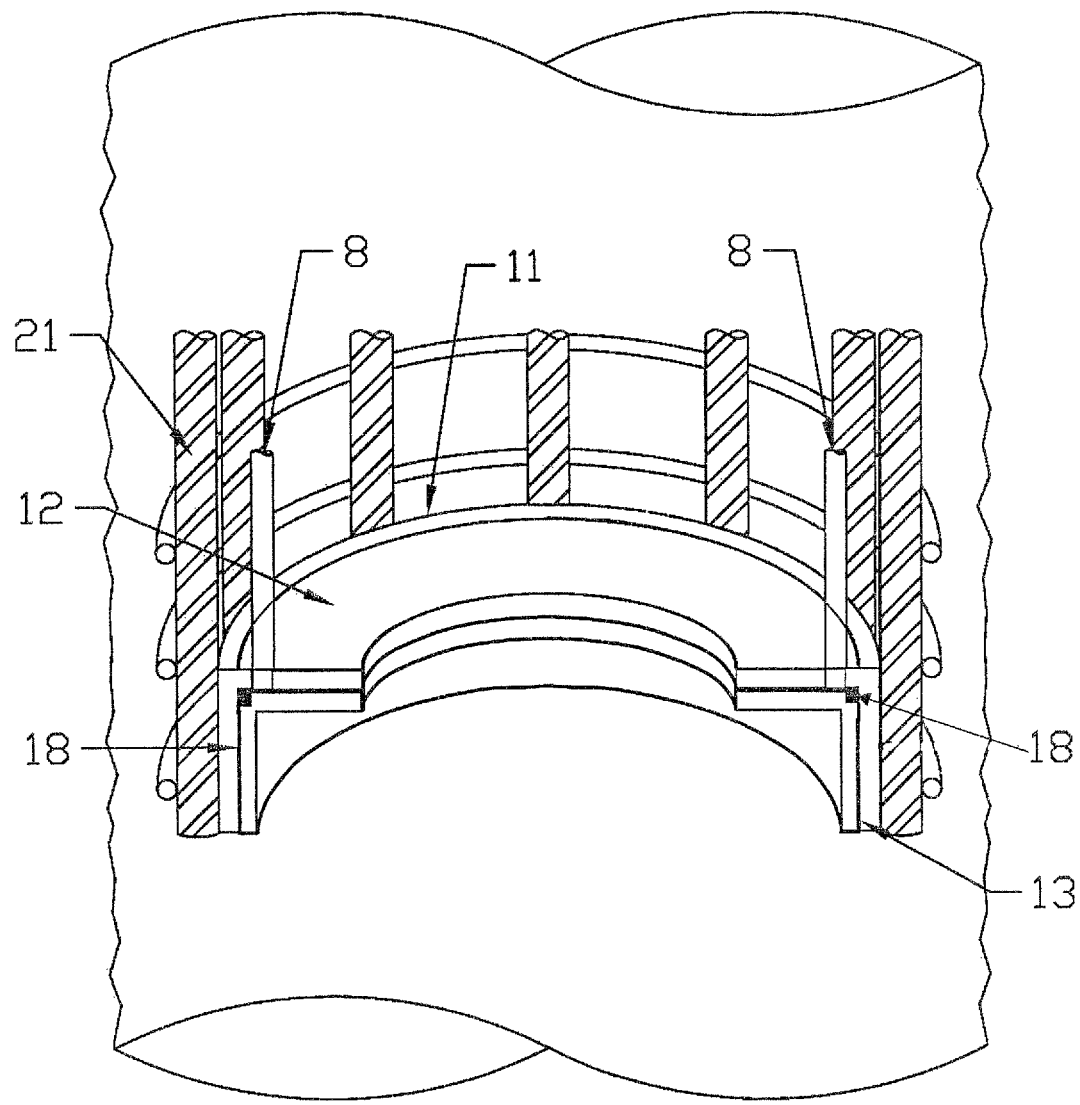
FIGS. 5A-5B show a sectional view of a specific embodiment of the present invention.
Figure 5B:
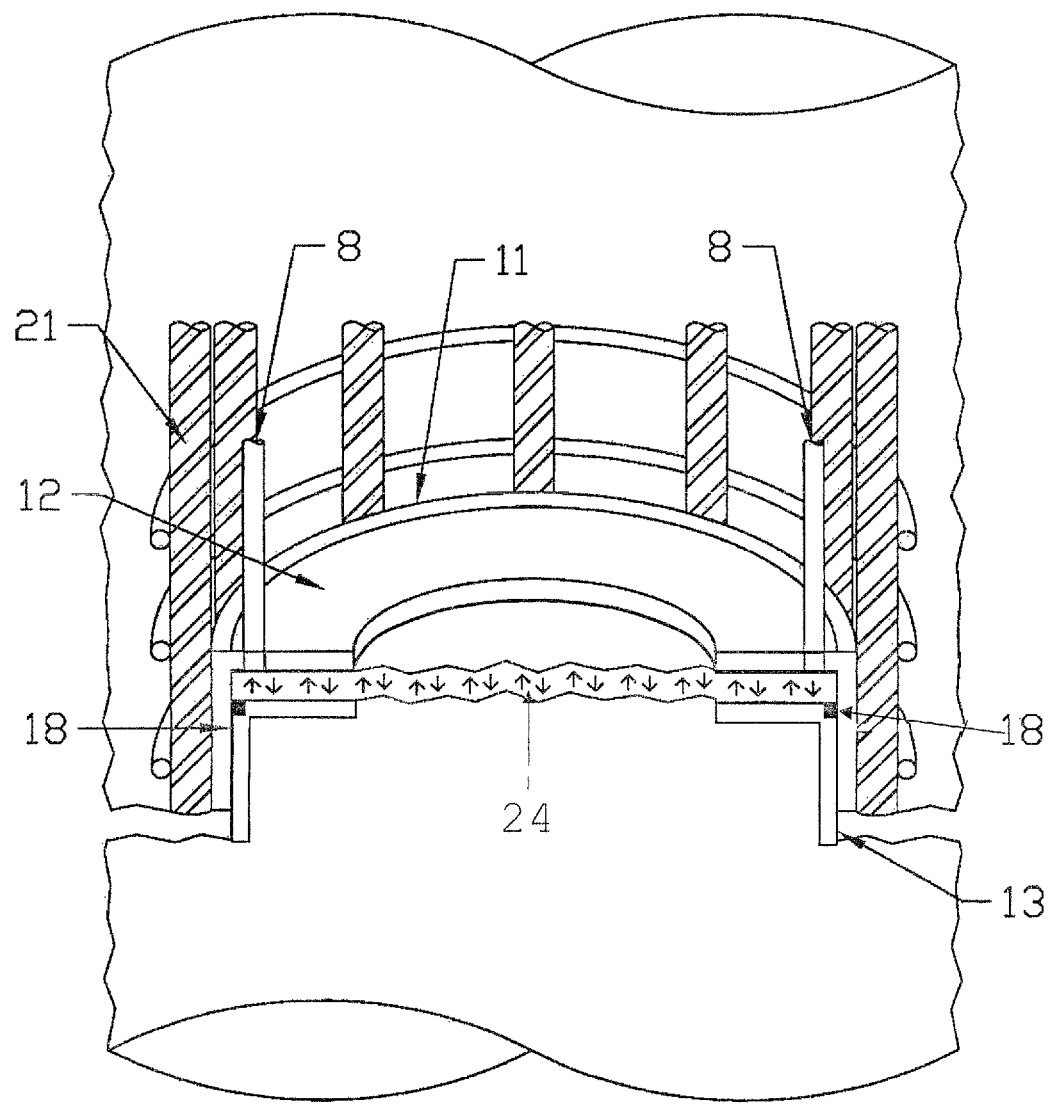

FIGS. 5A-5B show a sectional view of a specific embodiment of the present invention. In the embodiment shown, a hydraulic jack is provided in a ring shape. Two L-shaped pieces are used to create a plane for injection of pressurized fluid. In an embodiment, filler materials 6 capable of withstanding high pressure with minimal deformation as further described below can be included between the two L-shaped pieces such that the filler material augments one or both L-shaped piece much like shown in FIGS. 1A and 1B. Fluid access lines 8 are used to inject hydraulic fluid under pressure into the separation between the top L-shaped piece 12 and the bottom L-shaped piece. In the embodiment shown, an outer cylinder wall 11 is part of the top L-shaped piece 12 as is a top plate, such that the outer wall and top plate form the top L-shaped piece. The outer wall bounds the outside of any ring-shaped filler materials 6 used. The embodiment shown also includes a bottom plate and an inner wall formed integrally to form the bottom L-shaped piece. The outer wall can bound any filler materials 6 used above the bottom plate of the bottom L-shaped piece. The embodiment shown also includes seals 18 positioned to inhibit leaking of hydraulic fluid between the inner wall and the outer cylinder wall 11. In an embodiment, o-rings are used for the seals 18. The hydraulic jack can be attached to a rebar cage 21. As further discussed below, various structures can be used to attach the hydraulic jack to the rebar cage 21. As shown in FIG. 5A, the center of the top plate, the center of any ring-shaped filler material 6, and the center of the bottom plate are open to allow passage of materials through the hydraulic jack. The open center can allow concrete, grout, or other structural materials to be passed through the hydraulic jack. In an embodiment, the open center is used to form a contiguous pile having portions above and below the hydraulic jack, such that a portion of such a contiguous pile passes through the open center. As shown in FIG. 5B, a pile is formed that encompasses the rebar cage 21 and any ring-shaped filler materials 6.

In the embodiment shown in FIG. 5B, hydraulic fluid is injected under pressure via fluid access lines 8. The pressure from the hydraulic fluid pushes on the ring-shaped top plate and the bottom plate, and/or any filler materials 6 used, causing the top plate and bottom plate to separate. The top plate and bottom plate transfer the applied load to the pile. In the embodiment shown, the application of the load to the pile causes the pile to crack creating a void 24 in the pile. The void 24 is created in the open center of the ring-shaped jack. In the embodiment shown, the void 24 is contiguous with the separation between the top plate and bottom plate. Thus, the hydraulic fluid can flow from the separation into the void 24. The hydraulic fluid can fill all or part of the void 24. A self-sealing fluid capable of temporarily or permanently filling all or part of cracks emanating from the void 24 can be used. The hydraulic fluid fills or partially fills the void 24 under pressure such that the void 24 becomes an additional load applying area for applying a load to the pile. In an embodiment, use of the void 24 increases the surface area effectively normal to the direction of the load in contact with the pressurized fluid, such that the increased surface area allows a greater load to be applied to the pile. The pressurized fluid can be flushed out and replaced by pressurized grout, concrete, or other structural material, which can be allowed to cure so as to form a contiguous pile through the center of the jack. In a preferred embodiment, outer cylindrical wall 11 is designed such that the pressurized fluid will be contained within the volume formed within the outer cylindrical wall 11.

Referring to FIGS. 1A, 2A, and 5A, there is a separation between the top portion and the bottom portion of the jack, which is the separation between the top plate and the bottom plate of the two L-shaped pieces in FIG. 5A. For discussion, FIG. 5A will be used. Preferably, the amount of air or other compressible gas is minimized in this separate region, so that compressible bubbles are not introduced into the pressurized fluid system. In specific embodiments, paper, plastic, or other material that gives way when the pressurized fluid is introduced through fluid lines 8 can be positioned between the top plate and bottom plate. In an embodiment, a material can be positioned in the separation between the top plate and the bottom plate, such that if no testing is desired after the pile is poured around the jack then loading of the pile will not result in any compression of the separation region between the top plate and bottom plate. The separation region between the top plate and bottom plate can be referred to as a plane of weakness, which allows the pressurized fluid to enter the separation and push up on the top plate and push down on the bottom plate so that the pile can be fractured into a first, top, section and a second, bottom, section. Referring to the L-shaped pieces in FIG. 5A, preferably the length of the outer wall 11 is at least twice the amount of separation expected in the void 24. In specific embodiments, the amount of separation is less than 1 inch, or less than 2 inches. The L-shaped pieces can incorporate braces, such as from the bottom plate to the inner wall.

In an embodiment of the subject invention, grout, concrete, and/or other structural material is used as a pressurized fluid and/or to fill leaks, cracks, or voids in the load cell or the structure, such as a pile, under load. By using a grout, concrete, or other structural material to fill any cracks or voids in the jack, such as a separation between top and bottom portions, or other cracks or voids between top section of the pile and a bottom section of the pile once the top section is separated from the bottom section, the cured grout, concrete, or other structural materials, can securely maintain the separation of the top section and bottom section so as to have a construction pile that can be used after the grout, concrete, or other structural material has cured or otherwise is secured in place.

The self-sealing fluid can also be used, which is typically a chemical mix of friendly fibers, particulates, binders, polymers, and/or congealing agents that intertwine and clot to form an impervious seal. Commercial compounds with similar properties that can be used in embodiments of the subject invention include, but are not limited to, Slime® and AMERSEAL®. In an embodiment, the self-sealing fluid is used for load cells not incorporating seals 18, outer walls 11, top plates 12, bottom plates 13, and/or other components. In an embodiment, the self-sealing fluid seals leaks in the assembly and/or cracks in a structure being tested. In an embodiment, the fluid is pushed into the leak, crack, or void via the applied pressure. In an embodiment, the self-sealing fluid results in a permanent, flexible seal. In an embodiment, the self-sealing fluid fills or partially fills a void created by the action of a load cell. In an embodiment, a void created by action of the load cell is used as a load applying area during testing. In an embodiment, the self-sealing fluid is used to apply pressure during testing and then remains to seal leaks or fill cracks or voids once testing is complete. In an embodiment, a passage is formed in a filler material 6, outer walls 11, top plates 12, bottom plates 13, and/or other components of the load cell that allows the self-sealing fluid to reach a leak, crack, or void. In an embodiment, such a passage is intentionally formed.

In embodiments, fluid for pressurizing can provide self sealing properties via the fluid lines 8 that can obviate the need for seals to contain the high pressure. In specific embodiments, a self-sealing fluid can be used that can seal any leaks in the assembly. The use of a self-sealing fluid can reduce the need for tighter tolerances and/or other sealing mechanisms, such as o-rings. The use of self sealing fluid can reduce costs of manufacture and/or operation of embodiments of the ring cell. In other embodiments, seals 18 such as o-rings can be used where sealing is desired or necessary.

A concrete pile can completely surround the annular assembly. Concrete can be poured through the hole of the ring cell and fill the volume around the entire annular assembly. The outer wall of the ring cell can have a mechanism to be attached to a rebar cage 21. The mechanism can be one or more brackets.

Figure 6:
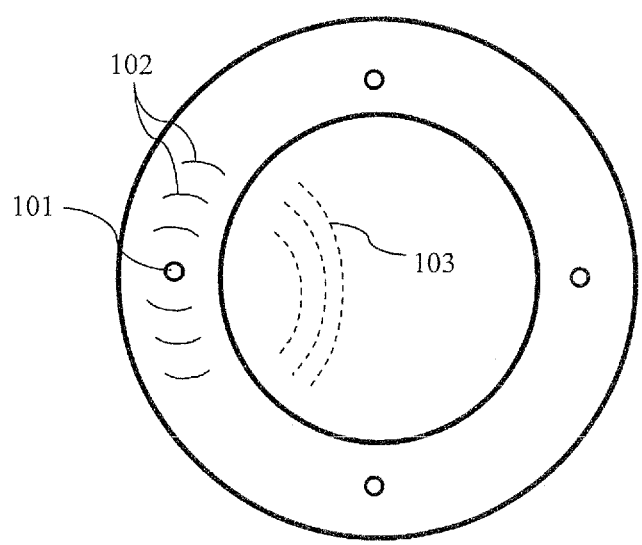
FIG. 6 shows a top view of a ring jack in accordance with an embodiment of the invention.

During testing of a pile, the concrete of the pile can be cracked by the expansion of the ring cell. FIG. 6 shows a top view of the ring jack with ports 101 for supplying pressurized fluid and/or hardening material. As the pressurized fluid is applied through ports 101 the pressurized fluid spreads out 102 and starts the fracturing (cracking) 103 of the pile, such that the pile separates into a first (top) section and a second (bottom) section. Accordingly, cracks or voids can appear in the pile. These voids can be filled with concrete, grout, and/or self-sealing fluid. These voids can also be filled by techniques known in the art, such as via supply or vent lines.

Figure 4:
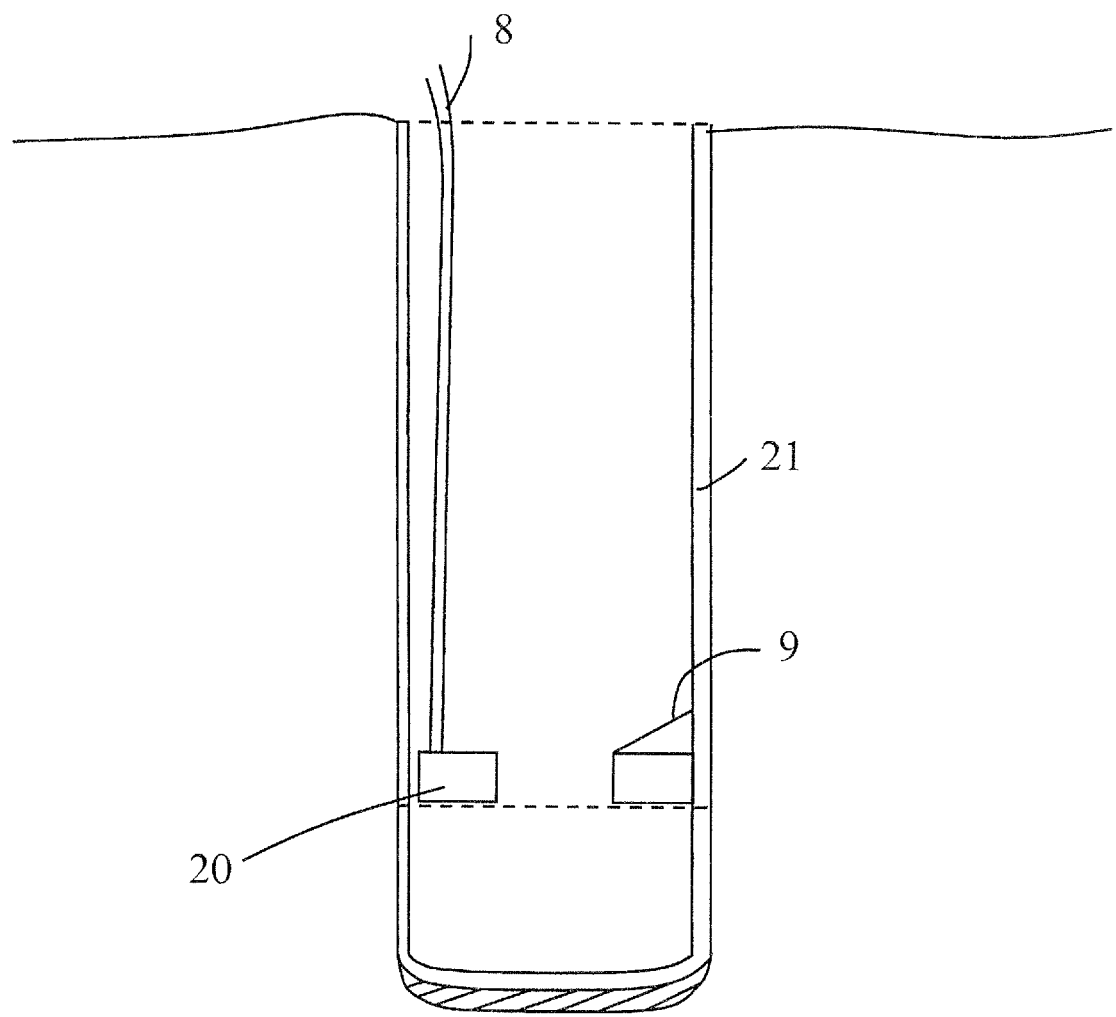
FIG. 4 shows an embodiment incorporating a ring cell within a pile.

In embodiments of the annular assembly, such as shown in FIGS. 1A, 2A, and 5A, a bladder is used to separate the top portion and bottom portion such that as pressurized fluid is pushed into the bladder, the bladder expands and separates the top portion and the bottom portion of the annular assembly, resulting in the fracture of the pile into a top section of pile and a bottom section of pile. In a specific embodiment, a separate supply line can supply pressurized fluid to void 24 once void 24 is formed and can supply material for hardening to void 24 once testing is complete. Alternatively, the bladder can be designed to rupture once void 24 is created so as to let pressurized fluid injected into the bladder enter void 24 and push up on the top section of the pile and push down on the bottom section of the pile. In specific embodiments, the ring cell can be positioned at, or near, the bottom of a drilled shaft. In other embodiments, the ring cell can be positioned in other portions of the pile, or in multiple locations in the pile. Referring to FIG. 4, an embodiment is shown where a ring cell 20 can be located within a pile. The ring cell 20 can be attached to a rebar cage 21 by, for example, a bracket 9. In one embodiment, the fluid supply lines 8 can supply grout to the bladder or separation between the top portion and bottom portion instead of pressurized water or hydraulic fluid. In another embodiment where pressurized water is used for testing, the water can be removed through an output line (not shown) as grout is supplied into the ring cell. In a further embodiment, the void 24 created between a section of the pile above the ring cell and a section of the pile below the ring cell can be filled in with, for example, grout or self-sealing fluid, as well as filling the expansion zone. Preferably, the ring cell is designed such that when expanded, the portion of the ring cell that tends to move up upon expansion of the ring cell (top) is sufficiently attached to the portion of the pile above the ring cell, the portion of the ring cell that tends to move down upon expansion of the ring cell (bottom) is sufficiently attached to the portion of the pile below the ring cell, and the top portion and bottom portion remain sufficiently interconnected to prevent relative lateral motion of the portion of the pile connected to the top portion and the portion of the pile connected to the bottom portion. In this way, once the separation between the top portion and bottom portion, and void 24, is filled with a material that prevents the top portion and bottom portion from coming back toward each other after expansion, the ring cell is coupled to the portion of the pile above the ring cell and the portion of the pile below the ring cell such as to retain the integrity of the pile as a single pile, rather than two pile sections floating with respect to each other either vertically or laterally.

One monitored measurement can be the volume of fluid used through the fluid lines into a separation between the top portion and bottom portion. The volume measurement can provide a means to monitor the opening of the annular assembly. According to embodiments of the present invention, many techniques to measure movement can be used. In one embodiment, the movement of a flexible piece can be measured as known in the art. In a second embodiment, a sonar system can monitor movement. In a third embodiment, a light based system (laser or photoelectric, for example) can be used to monitor distance. In a fourth embodiment, the amount of fluid supplied to the bladder and the pressure of the fluid can be monitored. The measurements may need to be calibrated due to a variety of factors such as hose expansion. In an embodiment, such measurements are monitored, tracked, and/or processed by a processing system as described below. In an embodiment, the functions of monitoring, tracking, and/or processing measurements are embodied on one or more computer-readable media as described below.

In an embodiment, one or more steps of a method for testing the load bearing capacity of one or more structures can be performed by a processing system as described below. In an embodiment, the functions of such a method are embodied on one or more computer-readable media as described below.

In an embodiment, one or more steps of a method of applying a load to a structure can be performed by a processing system as described below. In an embodiment, the functions of such a method are embodied on one or more computer-readable media as described below.

Aspects of the invention may be described in the general context of computer-executable instructions, such as program modules, being executed by a computer. Generally, program modules include routines, programs, objects, components, data structures, etc., that perform particular tasks or implement particular abstract data types. Such program modules can be implemented with hardware components, software components, or a combination thereof. Moreover, those skilled in the art will appreciate that the invention can be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, and numerous details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention can be practiced without these specific details. Computer systems, servers, work stations, and other machines can be connected to one another across a communication medium including, for example, a network or networks.

As one skilled in the art will appreciate, embodiments of the present invention can be embodied as, among other things: a method, system, or computer-program product. Accordingly, the embodiments can take the form of a hardware embodiment, a software embodiment, or an embodiment combining software and hardware. In an embodiment, the present invention takes the form of a computer-program product that includes computer-useable instructions embodied on one or more computer-readable media. Methods, data structures, interfaces, and other aspects of the invention described above can be embodied in such a computer-program product.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently. In an embodiment, non-transitory media are used.

The invention can be practiced in distributed-computing environments where tasks are performed by remote-processing devices that are linked through a communications network or other communication medium. In a distributed-computing environment, program modules can be located in both local and remote computer-storage media including memory storage devices. The computer-useable instructions form an interface to allow a computer to react according to a source of input. The instructions cooperate with other code segments to initiate a variety of tasks in response to data received in conjunction with the source of the received data.

The present invention can be practiced in a network environment such as a communications network. Such networks are widely used to connect various types of network elements, such as routers, servers, gateways, and so forth. Further, the invention can be practiced in a multi-network environment having various, connected public and/or private networks.

Communication between network elements can be wireless or wireline (wired). As will be appreciated by those skilled in the art, communication networks can take several different forms and can use several different communication protocols.

Embodiments of the subject invention can be embodied in a processing system. Components of the processing system can be housed on a single computer or distributed across a network as is known in the art. In an embodiment, components of the processing system are distributed on computer-readable media. In an embodiment, a user can access the processing system via a client device. In an embodiment, some of the functions or the processing system can be stored and/or executed on such a device. Such devices can take any of a variety of forms. By way of example, a client device may be a desktop or laptop computer, a personal digital assistant (PDA), an MP3 player, a communication device such as a telephone, pager, email reader, or text messaging device, or any combination of these or other devices. In an embodiment, a client device can connect to the processing system via a network. As discussed above, the client device may communicate with the network using various access technologies, both wireless and wireline. Moreover, the client device may include one or more input and output interfaces that support user access to the processing system. Such user interfaces can further include various input and output devices which facilitate entry of information by the user or presentation of information to the user. Such input and output devices can include, but are not limited to, a mouse, touch-pad, touch-screen, or other pointing device, a keyboard, a camera, a monitor, a microphone, a speaker, a printer, a scanner, among other such devices. As further discussed above, the client devices can support various styles and types of client applications.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to a person skilled in the art and are to be included within the spirit and purview of this application.

What is claimed is:

1. A method of applying a load to a pile, comprising:
    locating a top portion below a top section of a pile, wherein the top portion comprises a top cylindrical wall and a top plate, wherein the top portion is attached to the top section of the pile;
    locating a bottom portion below and proximate the top portion and above a bottom section of the pile, wherein the bottom portion comprises a bottom cylindrical wall and a bottom plate, wherein the bottom portion is attached to the bottom section of the pile, wherein at least a portion of the cross-section of the top portion and at least a portion of the cross-section of the bottom portion is open before casting the pile, wherein the at least a portion of the cross-section of the top portion is at least a portion of the top plate, wherein the at least a portion of the cross-section of the bottom portion is at least a portion of the bottom plate, and wherein the top section of the pile and the bottom section of the pile are contiguous through the open portion of the cross-section of the top portion and the open portion of the cross-section of the bottom portion;

injecting a pressurized fluid between the top portion and the bottom portion, wherein injecting the pressurized fluid between the top portion and the bottom portion causes the top portion and the bottom portion to be pushed apart, the top portion to push up on the top section of the pile with an initial upward force, the bottom portion to push down on the bottom section of the pile with an initial downward force, and at least one void to be created between the top section of the pile and the bottom section of the pile in a portion of the pile extending through the open portion of the cross-section of the top portion and the open portion of the cross-section of the bottom portion, wherein once the at least one void is created the pressurized fluid fills at least a portion of one or more of the at least one void, wherein the pressurized fluid that enters the at least a portion of one or more of the at least one void causes an additional upward force on the top section of the pile and an additional downward force on the bottom section of the pile, wherein before injecting the pressurized fluid between the top portion and the bottom portion, positioning at least a portion of the bottom cylindrical wall within the top cylindrical wall or positioning at least a portion of the top cylindrical wall within the bottom cylindrical wall, wherein at least a portion of the initial upward force is created by the pressurized fluid pushing on the top plate, wherein at least a portion of the initial downward force is created by the pressurized fluid pushing on the bottom plate.

2. A method of providing a plurality of piles for bearing a working load, comprising:

locating a plurality of piles in position in a strata for bearing a working load, wherein at least two of the piles incorporate a corresponding at least two load cells, wherein each load cell of the at least two load cells comprises:

a top portion located below a top section of a pile, wherein the top portion comprises a top cylindrical wall and a top plate; and a bottom portion located proximate the top portion, wherein the bottom portion comprises a bottom cylindrical wall and a bottom plate, wherein injection of a pressurized fluid between the top portion and the bottom portion causes a force tending to push the top portion and the bottom portion apart, and causes the top portion to push up on the top section of the pile, wherein at least a portion of the cross-section of the top portion and at least a portion of the cross-section of the bottom portion is open before casting the pile so as to allow the passage of materials from above the top portion to below the bottom portion, wherein the at least a portion of the cross-section of the top portion is at least a portion of the top plate, wherein the at least a portion of the cross-section of the bottom portion is at least a portion of the bottom plate, wherein if separation of top portion and bottom portion occurs, the top portion and bottom portion maintain relative lateral position during separation;

applying a corresponding at least two applied loads to the at least two piles via the corresponding at least two load cells;

measuring a corresponding at least two measured effects of the at least two applied loads on the at least two piles; and determining whether the plurality of piles meets at least one design criterion for bearing the working load based on the at least two applied loads and the at least two measured effects of the at least two applied loads on the at least two piles.

3. A load cell, comprising:

a top portion, wherein the top portion comprises a top cylindrical wall and a top plate; and a bottom portion located proximate the top portion, wherein the bottom portion comprises a bottom cylindrical wall and a bottom plate, wherein at least a portion of the cross-section of the top portion and at least a portion of the cross-section of the bottom portion is open so as to allow the passage of materials from above the top portion to below the bottom portion through the at least the portion of the cross-section of the top portion and the at least the portion of the cross-section of the bottom portion that is open, wherein the at least a portion of the cross-section of the top portion is at least a portion of the top plate, wherein the at least a portion of the cross-section of the bottom portion is at least a portion of the bottom plate, wherein the load cell is configured such that after casting a pile such that a top section of the pile is located above the top portion and a bottom section of the pile is located below the bottom portion and the top section of the pile and the bottom section of the pile are contiguous through the open portion of the cross-section of the top portion and the open portion of the cross-section of the bottom portion, injection of a pressurized fluid between the top portion and the bottom portion causes a force tending to push the top portion and the bottom portion apart, and causes the top portion to push up on the top section of the pile with an initial upward force and the bottom portion to push down on the bottom section of the pile with an initial downward force, and at least one void is created between the top section of the pile and the bottom section of the pile in a portion of the pile extending through the open portion of the cross-section of the top portion and the open portion of the cross-section of the bottom portion, wherein once the at least one void is created the pressurized fluid fills at least a portion of one or more of the at least one void, wherein the pressurized fluid that enters the at least a portion of one or more of the at least one void causes an additional upward force on the top section of the pile and an additional downward force on the bottom section of the pile, wherein the load cell is configured such that before injection of the pressurized fluid between the top portion and the bottom portion at least a portion of the bottom cylindrical wall is positioned within the top cylindrical wall or positioning at least a portion of the top cylindrical wall within the bottom cylindrical wall, wherein at least a portion of the initial upward force is created by the pressurized fluid pushing on the top plate, wherein at least a portion of the initial downward force is created by the pressurized fluid pushing on the bottom plate.

4. The load cell according to claim 3, wherein the load cell is configured such that before injection of the pressurized fluid between the top portion and the bottom portion, at least a portion of the top plate is adjacent at least a portion on the bottom plate and injection of the pressurized fluid between the top plate and the bottom plate causes the force tending to push the top portion and bottom portion apart.

5. The load cell according to claim 4, wherein if the at least a portion of the bottom cylindrical wall is positioned within the top cylindrical wall the pressurized fluid injected between the top plate and the bottom plate is confined by the top cylindrical wall, top plate, bottom plate, and the pile prior to the at least one void being created between the top section of the pile and the bottom section of the pile.

6. The load cell according to claim 4, wherein if the least a portion of the top cylindrical wall is positioned within the bottom cylindrical wall the pressurized fluid injected between the top plate and the bottom plate is confined by the bottom cylindrical wall, top plate, bottom plate, and the pile prior to the at least one void being created between the top section of the pile and the bottom section of the pile.

7. The method according to claim 1, wherein before injecting the pressurized fluid between the top portion and the bottom portion, at least a portion of the top plate is adjacent at least a portion on the bottom plate and injection of the pressurized fluid between the top plate and the bottom plate causes the force tending to push the top portion and bottom portion apart.

8. The method according to claim 7, wherein if the at least a portion of the bottom cylindrical wall is positioned within the top cylindrical wall the pressurized fluid injected between the top plate and the bottom plate is confined by the top cylindrical wall, top plate, bottom plate, and the pile prior to the at least one void being created between the top section of the pile and the bottom section of the pile.

9. The method according to claim 7, wherein if the least a portion of the top cylindrical wall is positioned within the bottom cylindrical wall the pressurized fluid injected between the top plate and the bottom plate is confined by the bottom cylindrical wall, top plate, bottom plate, and the pile prior to the at least one void being created between the top section of the pile and the bottom section of the pile.

10. The method according to claim 2, wherein the load cell is configured such that before injection of the pressurized fluid between the top portion and the bottom portion, at least a portion of the top plate is adjacent at least a portion on the bottom plate and injection of the pressurized fluid between the top plate and the bottom plate causes the force tending to push the top portion and bottom portion apart.

11. The method according to claim 10, wherein the pressurized fluid injected between the top plate and the bottom plate is initially confined by the top cylindrical wall, top plate, bottom plate, and the pile.

12. The method according to claim 10, wherein the pressurized fluid injected between the top plate and the bottom plate is initially confined by the bottom cylindrical wall, top plate, bottom plate, and the pile.

* * * * *

UNITED STATES PATENT AND TRADEMARK OFFICE
CERTIFICATE OF CORRECTION

| | |
|---|---|
| PATENT NO. | : 8,789,427 B2 |
| APPLICATION NO. | : 13/897612 |
| DATED | : July 29, 2014 |
| INVENTOR(S) | : John A. Hayes et al. |

It is certified that error appears in the above-identified patent and that said Letters Patent is hereby corrected as shown below:

In the Claims

Column 19,
Line 4, "if the least a" should read --if the at least a--.

Column 20,
Line 1, "if the least a" should read --if the at least a--.

Signed and Sealed this
Twenty-first Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,789,427 B2  
APPLICATION NO. : 13/897612  
DATED : July 29, 2014  
INVENTOR(S) : John A. Hayes et al.

Page 1 of 2

It is certified that error appears in the above-identified patent and that said Letters Patent is hereby corrected as shown below:

In the Drawings

Figure 2A,

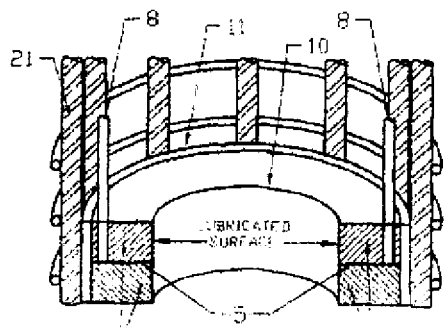

" should read

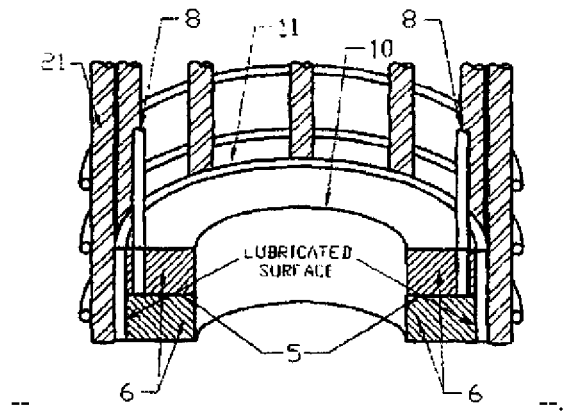

--.

Signed and Sealed this  
First Day of September, 2015

Michelle K. Lee  
*Director of the United States Patent and Trademark Office*

Figure 2C:
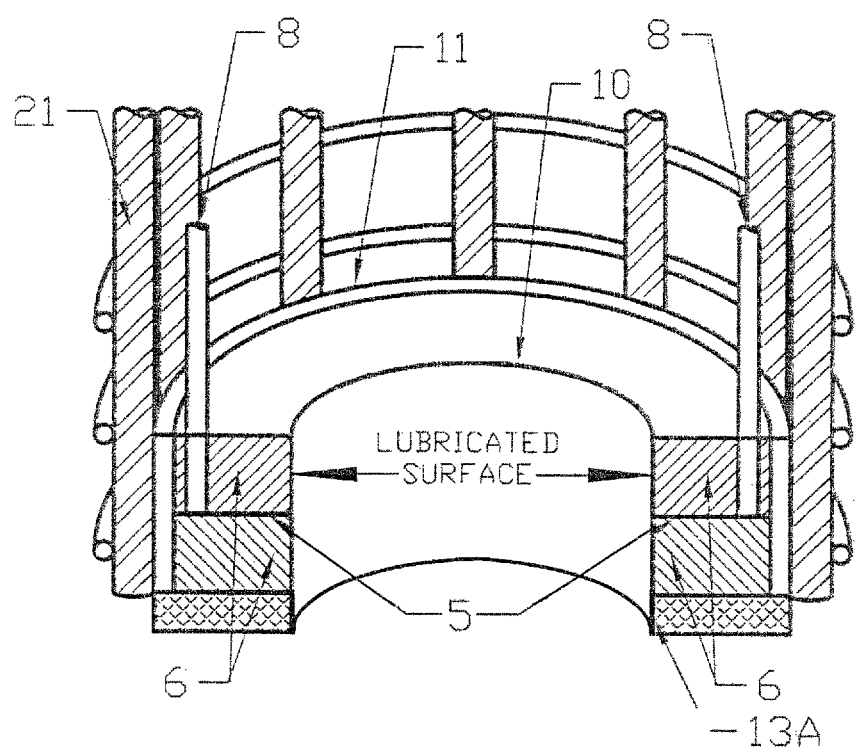

Figure 2B,
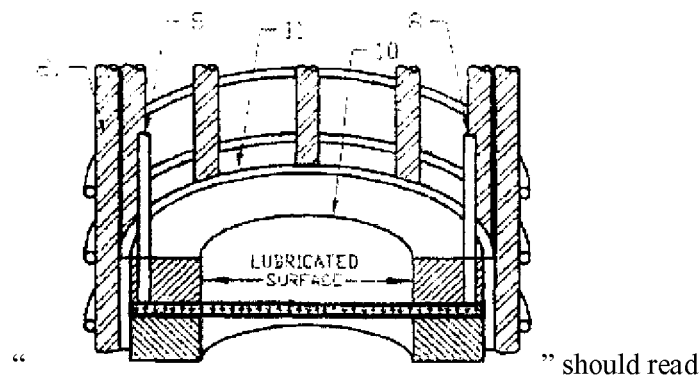
" 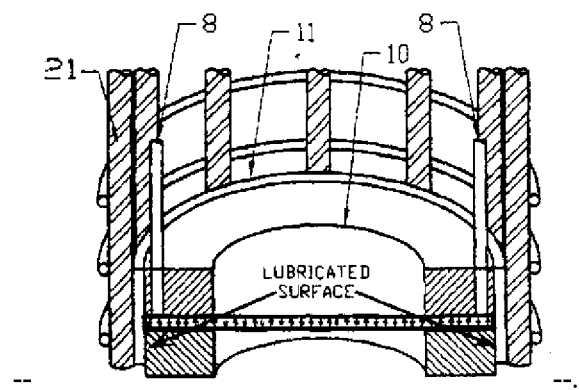 " should read
" 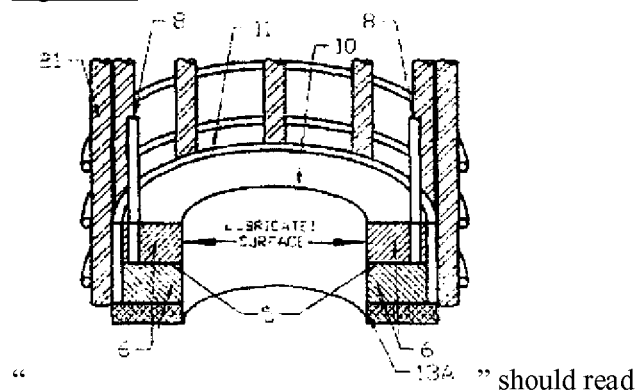 " should read
Figure 2C,
" 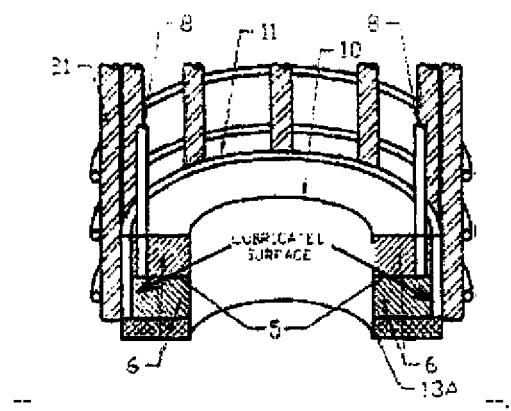 " should read